(12) United States Patent
Yoo et al.

(10) Patent No.: US 8,535,552 B2
(45) Date of Patent: Sep. 17, 2013

(54) METHOD OF EVALUATING CENTER SEGREGATION OF CONTINUOUS CAST SLAB

(75) Inventors: Sukhyun Yoo, Dangjin-gun (KR); Wonjae Cho, Dangjin-gun (KR); Jutae Choi, Seoul (KR); Kaeyoung Lee, Dangjin-gun (KR); Kyoungho So, Namwon-si (KR)

(73) Assignee: Hyundai Steel Company (KR)

( * ) Notice: Subject to any disclaimer, the term of this patent is extended or adjusted under 35 U.S.C. 154(b) by 0 days.

(21) Appl. No.: 13/310,394

(22) Filed: Dec. 2, 2011

(65) Prior Publication Data

US 2012/0074095 A1 Mar. 29, 2012

Related U.S. Application Data

(63) Continuation of application No. PCT/KR2010/004129, filed on Jun. 25, 2010.

(30) Foreign Application Priority Data

Jul. 27, 2009 (KR) ......................... 10-2009-0068464
Nov. 27, 2009 (KR) ......................... 10-2009-0116192
Nov. 27, 2009 (KR) ......................... 10-2009-0116198

(51) Int. Cl.
*C23F 1/00* (2006.01)

(52) U.S. Cl.
USPC ............. 216/84; 216/83; 252/79.1; 252/79.4; 426/78

(58) Field of Classification Search
None
See application file for complete search history.

(56) References Cited

U.S. PATENT DOCUMENTS 4,681,857 A * 7/1987 Funahashi et al. .............. 436/78
5,356,549 A * 10/1994 Takahashi et al. ............ 508/136

FOREIGN PATENT DOCUMENTS

| CN | 101344490 A | 1/2009 |
|---|---|---|
| JP | 06-088114 B2 | 11/1994 |
| JP | 09-196833 A | 7/1997 |
| JP | 09196833 * | 7/1997 |
| JP | 10-026632 A | 1/1998 |
| KR | 10-1989-0000392 B1 | 3/1989 |
| KR | 10-1995-0014077 B1 | 11/1995 |
| KR | 10-2002-0002672 A | 1/2002 |
| KR | 10-2002-0076340 A | 10/2002 |
| KR | 10-2004-0046121 A | 6/2004 |

OTHER PUBLICATIONS

K. Miyamura et al., "Development of Segregation Etch Print Method and Its Application to Investigation of CC Slab Segregation", Trans. Iron Steel Inst. Jpn. vol. 24, No. 9, pp. 718-725, Sep. 1984.*

(Continued)

*Primary Examiner* — Lan Vinh
*Assistant Examiner* — Jiong-Ping Lu
(74) *Attorney, Agent, or Firm* — Knobbe Martens Olson & Bear, LLP

(57) ABSTRACT

A method for evaluating center segregation of a continuous cast slab is provided. The method of the present invention includes (A) creating a center segregation image of a slab using an etching solution comprising a picric acid ($C_6H_3N_3O_7$), a cupric chloride ($CuCl_2$), sodium laurylbenzenesulfonate ($C_{18}H_{29}SO_3Na$) and the remainder of distilled water; and (B) evaluating the center segregation of a slab by scanning the image and applying the following Formula. The method creates an image of center segregation even for low-carbon steel having carbon (C) in an amount of 0.04 wt % or less as well as ultra low-sulfur steel having sulfur (S) in an amount of 50 ppm or less.

12 Claims, 5 Drawing Sheets

(56) References Cited

OTHER PUBLICATIONS

G.F. Vander Voort, "Wetting Agents in Metallography", Materials Characterization vol. 35, 1995, pp. 135-137.*

K. Miyamura et al. "New Evaluation Techniques of Segregation in Continuously Cast Steel", Trans. Iron Steel Inst. Jpn., vol. 24, No. 11, pp. 883-890, Nov. 1984.*

International Search Report dated Feb. 1, 2011 of PCT/KR2010/004129 and its English Translation (4 pages).

Written Opinion dated Feb. 1, 2011 of PCT/KR2010/004129 (3 pages).

Chinese First Office Action dated May 6, 2013 of corresponding Chinese Patent Application No. 201080024771.4—15 pages.

* cited by examiner

PORE

CENTER SEGREGATION

METHOD OF EVALUATING CENTER SEGREGATION OF CONTINUOUS CAST SLAB

RELATED APPLICATION

This application is a continuation application under 35 U.S.C. §365(c) of International Application No. PCT/KR2010/004129, filed Jun. 25, 2010 designating the United States. This application further claims the benefit of the earlier filing date under 35 U.S.C. §365(b) of Korean Patent Application No. 10-2009-0068464 filed Jul. 27, 2009, Korean Patent Application No. 10-2009-0116192 filed Nov. 27, 2009 and Korean Patent Application No. 10-2009-0116198 filed Nov. 27, 2009. This application incorporates herein by reference the International Application No. PCT/KR2010/004129 and the Korean Patent Application Nos. 10-2009-0068464, 10-2009-0116192 and 10-2009-0116198 in their entirety.

TECHNICAL FIELD

The present disclosure relates to a method of evaluating center segregation of a continuous cast slab.

BACKGROUND ART

Molten steel treated to have a desired composition and temperature during a steel-making process, is cooled while passing through a continuous casting machine and solidified into a slab.

In the continuous casting machine, first, molten steel is formed into a solidification shell while passing through a water-cooling mold, and then residual molten steel is completely solidified by injecting cooling water while passing through a strand into a slab.

SUMMARY

An aspect of the present invention is to provide a method of evaluating center segregation of continuous cast slab, which can quickly obtain a high-resolution center segregation image of a slab using an etching solution containing predetermined components.

Another aspect of the present invention is to provide a method of evaluating center segregation of continuous cast slab, which can quickly obtain a high-resolution center segregation image of a slab even when the slab is made of ultra low-sulfur steel having sulfur (S) in an amount of 50 ppm or less or low-carbon steel having carbon (C) in an amount of 0.04 wt % or less.

Still another aspect of the present invention is to provide a method of evaluating center segregation of continuous cast slab, which can quickly and accurately obtain and evaluate a high-resolution center segregation image of a slab.

An aspect of the present invention provides a method of evaluating center segregation of a continuous cast slab, including the steps of: immersing a slab into an etching solution to etch the slab, the etching solution comprising a predetermined amount of picric acid ($C_6H_3N_3O_7$), a predetermined amount of cupric chloride ($CuCl_2$), a predetermined amount of sodium laurylbenzenesulfonate ($C_{18}H_{29}SO_3Na$), a predetermined amount of ethanol ($C_2H_5OH$) and a remainder of distilled water; washing the etched slab and then drying the washed slab; applying silicone grease onto the surface of the dried slab; wiping off the silicone grease and then grinding the etched surface of the slab, the etched surface thereof being coated with the silicone grease; attaching transparent adhesive tape onto the grinded etched surface of the slab; detaching the transparent adhesive tape from the grinded etched surface of the slab and attaching the transparent adhesive tape onto paper; and evaluating center segregation of the slab based on the obtained results.

Here, the amount of the picric acid ($C_6H_3N_3O_7$) may be 1.5~2.0 wt %, the amount of the cupric chloride ($CuCl_2$) may be 0.5~1.0 wt %, and the amount of the sodium laurylbenzenesulfonate ($C_{18}H_{29}SO_3Na$) may be 1.0~3.0 wt %.

Further, the amount of the ethanol ($C_2H_5OH$) may be more than 0 vol % and 10 vol % or less.

Another aspect of the present invention provides a method evaluating center segregation of a continuous cast slab, comprising the steps of: immersing a slab sample into an etching solution and then heating the etching solution, the etching solution comprising picric acid ($C_6H_3N_3O_7$), cupric chloride ($CuCl_2$), sodium laurylbenzenesulfonate ($C_{18}H_{29}SO_3Na$) and a remainder of distilled water; washing the etched slab sample and then drying the washed slab sample; applying silicone grease onto the surface of the dried slab sample; wiping off the silicone grease and then grinding the silicone grease-applied surface of the slab sample; and attaching transparent adhesive tape onto the grinded etched surface of the slab sample, detaching the transparent adhesive tape from the grinded etched surface of the slab sample, and then attaching the transparent adhesive tape onto paper to form a solidification structure image.

Here, the amount of the picric acid ($C_6H_3N_3O_7$) may be 1.5~2.0 wt %, the amount of the cupric chloride ($CuCl_2$) may be 0.5~1.0 wt %, and the amount of the sodium laurylbenzenesulfonate ($C_{18}H_{29}SO_3Na$) may be 1.0~3.0 wt %.

Further, the temperature of the etching solution may be 30~80° C.

Further, the temperature of the etching solution may be 50~80° C.

Further, the slab may be made of low-carbon steel having carbon (C) in an amount of 0.04 wt % or less or ultra low-sulfur steel having sulfur (S) in an amount of 50 ppm or less.

Still another aspect of the present invention provides a method of evaluating center segregation of a continuous cast slab, comprising the steps of: (A) creating a center segregation of a slab into an image; and (B) evaluating the center segregation of a slab by scanning the image and applying the following Formula: $2.1+(0.15Y-8.7X)/(2.9\times10^7)$ wherein X is an area of center segregated particles, and Y is an area of residual segregated particles excluding the center segregated particles.

Here, the step (A) may include the steps of: immersing a slab sample into an etching solution and then heating the etching solution, the etching solution comprising picric acid ($C_6H_3N_3O_7$), cupric chloride ($CuCl_2$), sodium laurylbenzenesulfonate ($C_{18}H_{29}SO_3Na$) and a remainder of distilled water; washing the etched slab sample and then drying the washed slab sample; applying silicone grease onto the surface of the dried slab sample; wiping off the silicone grease and then grinding the silicone grease-applied surface of the slab sample; and attaching transparent adhesive tape onto the grinded etched surface of the slab sample, detaching the transparent adhesive tape from the grinded etched surface of the slab sample, and then attaching the transparent adhesive tape onto paper to form a segregation image.

Further, the amount of the picric acid ($C_6H_3N_3O_7$) may be 1.5~2.0 wt %, the amount of the cupric chloride ($CuCl_2$) may be 0.5~1.0 wt %, and the amount of the sodium laurylbenzenesulfonate ($C_{18}H_{29}SO_3Na$) may be 1.0~3.0 wt %.

Further, the temperature of the etching solution may be 30~80° C.

Further, the temperature of the etching solution may be 50~80° C.

Further, the step (B) may include the steps of: creating an electronic file by scanning the image; and measuring an area of center segregated particles, and an area of residual segregated particles excluding the center segregated particles.

According to embodiments of the present invention, since a high-resolution center segregation image of a slab can be obtained even when the slab is made of ultra low-sulfur steel having sulfur (S) in an amount of 50 ppm or less, the center segregation of the slab can be easily observed by the naked eye, and the center segregation thereof can be rapidly evaluated relative to the evaluation of the center segregation using electron probe macroanalysis (EPMA), and the time necessary for evaluating the center segregation thereof using the method in accordance with embodiments of the present invention is equal to or less than $1/10$ of the time necessary for evaluating the center segregation thereof using the electron probe macroanalysis (EPMA), and thus the results can be quickly used for casting process.

Further, according to embodiments of the present invention, the high resolution solidification structure and center segregation image of a slab can be obtained even when the slab is made of low-carbon steel having carbon (C) in an amount of 0.04 wt % or less. Therefore, the process abnormality occurring when low-carbon steel is cast can be quickly detected and then dealt with.

Furthermore, according to embodiments of the present invention, the high-resolution solidification structure and center segregation image of a slab can be obtained even when the slab is made of low-carbon steel having carbon (C) in an amount of 0.04 wt % or less as well as ultra low-sulfur steel having sulfur (S) in an amount of 50 ppm or less, and the high resolution solidification structure and center segregation image thereof can also be quantified. Therefore, the process abnormalities occurring during casting of low-carbon steel can be quickly detected and then dealt with, thus the product reliability is increased, and the degree of consumer satisfaction is improved.

EMBODIMENTS

Hereinafter embodiments of the present invention will be described in detail with reference to the accompanying drawings.

In the method of evaluating center segregation of a continuous cast slab according to a first embodiment of the present invention, a slab is immersed into an etching solution including predetermined components to etch the slab to corrode the center segregation of the slab, the etched surface of the slab is grinded with sandpaper to allow powder to permeate into the corroded center segregation, and then transparent adhesive tape is attached to corroded center segregation to allow the powder to stick to the transparent adhesive tape to visualize the segregation.

In a continuous casting process, when molten steel is solidified while it is cooled by a strand, solute elements are discharged from solids having lower solubility than that of liquids and concentrated between dendritic crystals, thus causing a microsegregation phenomenon of a slab.

Figure 1:
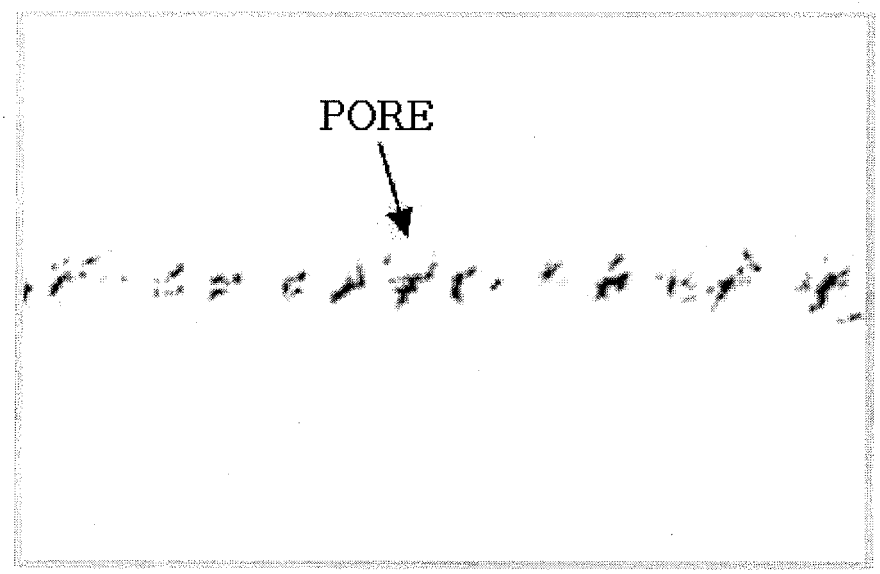
FIG. 1 is a view showing pores formed in the center of thickness of a slab.
Figure 2:
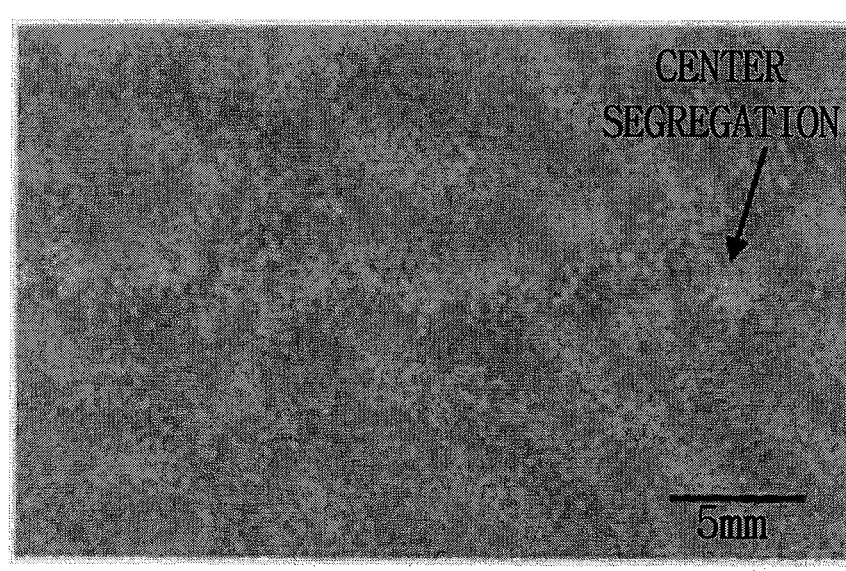
FIG. 2 is a view showing the center segregation phenomenon of a slab.

Due to the microsegregation phenomenon, as shown in FIG. 1, pores are formed at the center of thickness of a slab by solidification contraction at the time of solidification completion, so that microsegregation particles are sucked between dendritic crystals by the negative pressure in the pores, with the result that, as shown in FIG. 2, the components, such as sulfur, phosphorus, manganese, carbon and the like, concentrated in residual molten steel are accumulated at the central region of thickness of a slab, thereby causing a center segregation phenomenon.

When the center segregation phenomenon seriously occurs in the slab, center segregation remains in a coil that is a final product. Since the center segregation remaining in the coil is harder than other matrices, the weldability of the slab deteriorates, or, when the slab is formed into a steel pipe, such as an oil transport pipe, and then used, the steel sheet is cracked by the center segregation of the slab, thus damaging the steel pipe.

This center segregation of the slab must be reduced because it causes hydrogen-induced cracking and weld cracking. For this purpose, it is necessary to accurately grasp the level of center segregation.

In order to evaluate the center segregation of a slab, it is necessary to visualize the center segregation thereof. As methods of visualizing center segregation, a sulfur printing method, a macroetching method and an electron probe macroanalysis (EPMA) method are frequently used.

The sulfur printing method is a method of visualizing center segregation by attaching photographic paper coated with a dilute sulfuric acid solution to a grinded slab, detaching the photographic paper from the grinded slab and then drying this photographic paper. The principle of the sulfur printing method is that sulfur (S) segregated at the center of a slab reacts with sulfuric acid to generate $H_2S$ gas, and this $H_2S$ gas is exposed to light on the photographic paper, thus forming black spots on the photographic paper.

Figure 3:
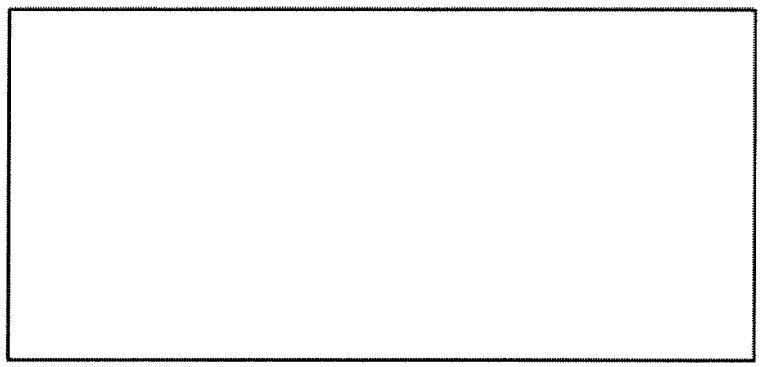
FIGS. 3 to 5 are views showing the results of analyzing a slab made of ultra low-sulfur steel having sulfur (S) in an amount of 50 ppm or less using a sulfur printing method, an electron probe macroanalysis (EPMA) method and a center segregation evaluating method of a first embodiment of the present invention, respectively.
Figure 6:
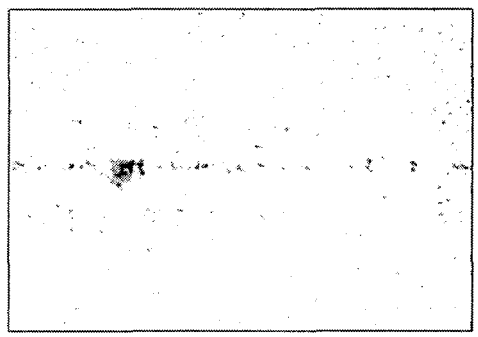
FIG. 6 (a) shows the result of analyzing a slab made of general steel having sulfur (S) in an amount of 200 ppm using a sulfur printing method, and FIG. 6 (b) shows a slab made of ultra low-sulfur steel having sulfur (S) in an amount of 24 ppm using a sulfur printing method.
Figure 6:
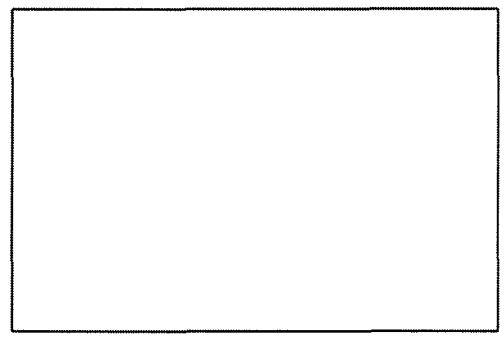

However, in the sulfur printing method, since the amount of $H_2S$ gas generated from ultra low-sulfur steel having sulfur (S) in an amount of 50 ppm or less that is used to make most oil transport pipes, center segregation is not visualized, and the resolution of the image is very low even though the image of the center segregation is created (refer to FIGS. 3 and 6).

The principle of the macroetching method is that a slab sample is immersed into a mixed solution in which water and hydrochloric acid are mixed at a ratio of 1:1 to etch the slab sample to visualize the solidification structure and segregation thereof.

Figure 8:
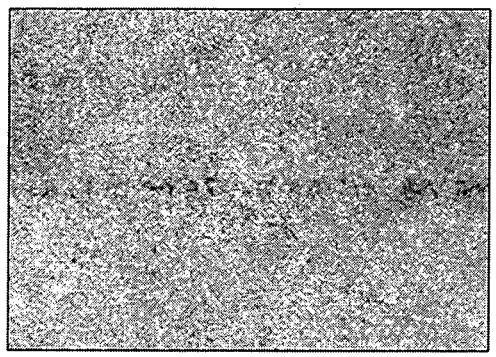
FIGS. 8 and 9 are views showing the results of analyzing a slab made of medium-carbon steel having carbon (C) in an amount of 0.046 wt % and a slab made of low-carbon steel having carbon (C) in an amount of 0.002 wt % using a macroetching method and a center segregation evaluating method of a second embodiment of the present invention, respectively.
Figure 8:
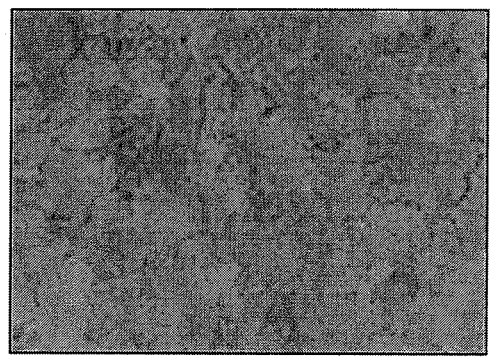

However, in the macroetching method, since carbon (C) is excessively reacted with hydrochloric acid (HCl), in the case of low-carbon steel having carbon (C) in an amount of 0.04 wt % or less, the resolution of the segregation image is very low, and thus it is difficult to observe the segregation (refer to FIG. 8).

Unlike the above-mentioned two methods, the electron probe macroanalysis (EPMA) method is a method of most accurately evaluating the center segregation of a slab. This EPMA method is used to determine the quantitative index of center segregation because it can conduct quantitative analysis of all kinds of steels on ppm.

However, in the EPMA method, since it takes about 12 hours to treat and analyze a slab sample, it requires too much time to create an image of center segregation.

Therefore, a novel etching solution is prepared in order to form an image of a high-resolution center segregation image.

The novel etching solution serves to quickly form a high-resolution center segregation image of a slab even when the slab is made of ultra low-sulfur steel having sulfur (S) in an amount of 50 ppm or less or low-carbon steel having carbon (C) in an amount of 0.04 wt % or less.

Specifically, first, a slab is immersed into an etching solution including predetermined components for a predetermined amount of time to etch the slab.

The etching solution includes a predetermined amount of picric acid ($C_6H_3N_3O_7$), a predetermined amount of cupric chloride ($CuCl_2$), a predetermined amount of sodium laurylbenzenesulfonate ($C_{18}H_{29}SO_3Na$), a predetermined amount of ethanol ($C_2H_5OH$) and a remainder of distilled water.

Here, in some embodiments, the amount of the picric acid ($C_6H_3N_3O_7$) be 1.5~2.0 wt %, the amount of the cupric chloride ($CuCl_2$) be 0.5~1.0 wt %, and the amount of the sodium laurylbenzenesulfonate ($C_{18}H_{29}SO_3Na$) be 1.0~3.0 wt %. In one embodiment, the amount of the ethanol ($C_2H_5OH$) is more than 0 vol % and 10 vol % or less.

Hereinafter, the functions and numerical limitations of the components included in the etching solution of embodiments of the present invention will be described.

Picric acid ($C_6H_3N_3O_7$): 1.5~2.0 wt %

When the amount thereof is less than 1.5 wt %, it takes 2 hours or more to etch the slab, and thus etching time increases. When the amount thereof is more than 2.0 wt %, spots are formed by insoluble precipitates. Therefore, the amount thereof is limited to a range of 1.5~2.0 wt %.

Cupric chloride ($CuCl_2$): 0.5-1.0 wt %

When the amount thereof is less than 0.5 wt %, the resolution of the etched slab decreases, and, when the amount thereof is more than 1.0 wt %, the slab is excessively etched. Therefore, the amount thereof is limited to a range of 0.5~1.0 wt %.

Sodium laurylbenzenesulfonate ($C_{18}H_{29}SO_3Na$): 1.0~3.0 wt %

When benzyldimethyltetradecylammonium chloride ($C_{23}H_{42}ClN$) is used as a surfactant, adhesive reactants were formed on the etching surface of a slab, and thus etching reaction may be obstructed.

Therefore, in embodiments of the present invention, sodium laurylbenzenesulfonate ($C_{18}H_{29}SO_3Na$) is used as a surfactant. When the amount thereof is less than 1.0 wt %, the etching rate of a slab decreases. When the amount thereof is more than 3.0 wt %, it is oversaturated, and thus precipitates are generated. Therefore, the amount thereof is limited to a range of 1.0~3.0 wt %.

Ethanol ($C_2H_5OH$): more than 0 vol % and 10 vol % or less

Ethanol ($C_2H_5OH$) is advantageous in removing all traces after etching because it is easily volatilized. However, the amount thereof is more than 10 vol %, the etching rate of a slab decreases, and the concentration of an etching solution is changed by the volatilization of ethanol. Therefore, the amount thereof is limited to a range of more than 0 vol % and 10 vol % or less.

Meanwhile, an etching solution including the above components and a remainder of distilled water is prepared, and then a slab is immersed into the etching solution for a predetermined amount of time to etch the slab. The distilled water is mixed in the etching solution at room temperature.

The slab is prepared by grinding in advance. The slab is immersed in the etching solution for two hours or less. When the slab is immersed in the etching solution for more than two hours, the slab is excessively etched, and thus the resolution thereof decreases rapidly.

Subsequently, the etched slab is washed with water using a brush to remove adherents therefrom, and then the washed slab is dried by hot air.

Thereafter, silicone grease is applied onto the surface of the dried slab to fill the recesses formed by corroding the slab using the etching solution with the silicone grease.

After a predetermined amount of time, for example, after 1~3 minutes, the silicone grease is wiped off, and then the etched surface of the slab coated with the silicone grease is uniformly grinded using fine sandpaper having a grit number of 800 or higher.

The surface roughness of the sandpaper is determined depending on the size of abrasive grains of the sandpaper. In this case, as the surface roughness thereof increases, the resolution thereof decreases. Therefore, if possible, sandpaper having a grit number of 800 or higher may be used.

When the recesses of the slab are filled with fine powder produced during the grinding process, the powder is mixed with the silicone grease to provide light and darkness.

Thereafter, a transparent adhesive tape is attached onto the grinded etched surface of the slab. Thus, the powder sticks to the transparent adhesive tape to create an image of segregation. If the transparent adhesive tape is attached onto white paper and then the white paper is scanned, as shown in FIG. 5, center segregation can be observed with the naked eye.

In conclusion, center segregation can be easily evaluated by the results obtained by attaching the transparent adhesive tape onto the white tape and then scanning the white paper.

Figure 4:
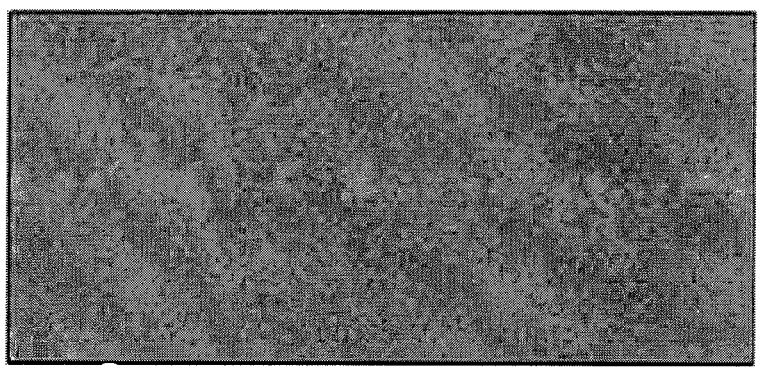
Figure 5:
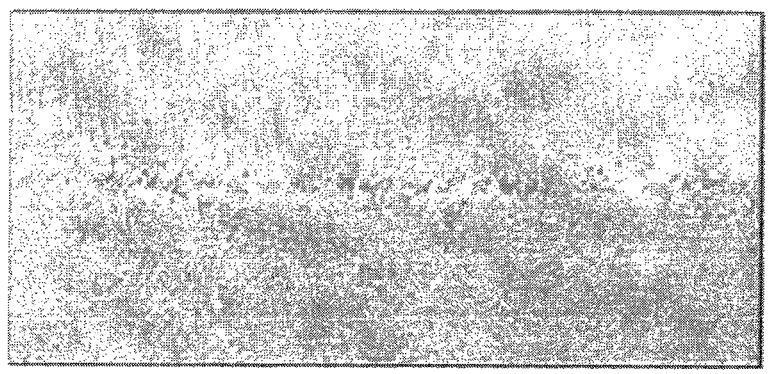

FIGS. 3 to 5 are views showing the results of analyzing a slab made of ultra low-sulfur steel having sulfur (S) in an amount of 50 ppm or less using a sulfur printing method, an electron probe macroanalysis (EPMA) method and a center segregation evaluating method of a first embodiment of the present invention, respectively.

As shown in FIG. 3, according to the sulfur printing method, the center segregation image of the slab made of ultra low-sulfur steel can be hardly obtained, so that it is very difficult to observe with the naked eye.

As shown in FIG. 4, according to the EPMA method, a high-resolution center segregation image can be obtained, but there is a problem in that it takes about 12 hours to treat and analyze a sample.

In contrast, in the case of the method of evaluating center segregation of a continuous cast slab according to embodiments of the present invention, as shown in FIG. 5, since a high-resolution center segregation image of a slab can be obtained even when the slab is made of ultra low-sulfur steel having sulfur (S) in an amount of 50 ppm or less, the center segregation of the slab can be observed with the naked eye, and the center segregation thereof can be evaluated for a short period of time which is equal to or smaller than 1/10 of the time for the EPMA method, thus the results can be quickly utilized in casting operation work.

In the method of evaluating center segregation of a continuous cast slab according to a second embodiment of the present invention, a slab sample is immersed into an etching solution and then heated to corrode the segregation of the slab sample, the etched surface of the slab sample is grinded by sandpaper to allow powder to permeate into the selectively corroded segregation, and then transparent adhesive tape is attached to the slab sample to allow the powder to stick to the transparent adhesive tape, thereby creating an image of the segregation.

The method of the second embodiment is different from the method of the first embodiment in that the etching solution does not include ethanol and in that the method of the second embodiment further includes a process of immersing the slab sample into the etching solution and then heating the etching solution.

In the above-mentioned method of the first embodiment, the etching solution includes ethanol in order to increase an etching efficiency. However, in the method of the second embodiment, ethanol is not used. The reason for this is that the heating may not be effective because ethanol has a boiling point of 65° C.

Specifically, first, a slab is immersed into an etching solution including predetermined components for a predetermined amount of time and then heated to etch the slab.

The etching solution includes a predetermined amount of picric acid ($C_6H_3N_3O_7$), a predetermined amount of cupric chloride ($CuCl_2$), a predetermined amount of sodium laurylbenzenesulfonate ($C_{18}H_{29}SO_3Na$), and a remainder of distilled water.

Here, in one embodiment, the amount of the picric acid ($C_6H_3N_3O_7$) be 1.5~2.0 wt %, the amount of the cupric chloride ($CuCl_2$) be 0.5~1.0 wt %, and the amount of the sodium laurylbenzenesulfonate ($C_{18}H_{29}SO_3Na$) be 1.0~3.0 wt %.

Since the functions and numerical limitations of the components included in the etching solution of the second embodiment of the present invention are the same as those of the components included in the etching solution of the first embodiment of the present invention, descriptions thereof will be omitted.

The temperature of the etching solution is 30~80° C. The slab sample is immersed into the etching solution and then the etching solution is heated in order to accelerate an etching reaction. When the temperature of the etching solution is lower than 30° C., the etching reaction is slow. Further, when the temperature thereof is higher than 80° C., poisonous gases are generated, and dangers are caused by high-temperature vapor. Therefore, in one embodiment, the temperature of the etching solution for accelerating the etching reaction be 50~80° C.

The immersion of the slab sample into the etching solution is conducted for two hours or less. The reason for this is that, when the immersion thereof is conducted for more than two hours, the slab sample is overetched, thus rapidly decreasing resolution.

Meanwhile, the slab sample is prepared by grinding in advance.

Subsequently, the etched slab sample is washed with flowing water using a brush to remove adherents therefrom, and then the washed slab is dried by hot air.

Thereafter, silicone grease is applied onto the surface of the dried slab to fill the recesses formed by corroding the slab using the etching solution with the silicone grease.

After a predetermined amount of time, for example, after 1~3 minutes, the silicone grease is wiped off, and then the etched surface of the slab coated with the silicone grease is uniformly grinded using fine sandpaper having a grit number of 800 or higher.

The surface roughness of the sandpaper is determined depending on the size of abrasive grains of the sandpaper. In this case, as the surface roughness thereof increases, the resolution thereof decreases. Therefore, if possible, sandpaper having a grit number of 800 or higher may be used.

When the recesses of the slab are filled with fine powder produced during the grinding process, the powder is mixed with the silicone grease to provide light and darkness.

Thereafter, a transparent adhesive tape is attached onto the grinded etched surface of the slab. Thus, the powder sticks to the transparent adhesive tape to create an image of a solidification structure. If the transparent adhesive tape is attached onto white paper and then the white paper is scanned, a solidification structure image can be observed with the naked eye.

In conclusion, center segregation can be easily evaluated by the results obtained by attaching the transparent adhesive tape onto the white tape and then scanning the white paper.

Table 1 shows the results of applying the center segregation evaluating method to a slab sample made of low-carbon steel having carbon (C) in an amount of 0.002 wt % depending on the conditions of an etching solution.

Experimental condition: an etching solution was heated to 70° C., and a slab sample was immersed in the etching solution for two hours.

TABLE 1

| Class. | Picric acid (wt %) | Cupric chloride (wt %) | Surfactant (wt %) | Solidification structure resolution (after 2 hour-immersion | Remarks |
| --- | --- | --- | --- | --- | --- |
| 1 | 1.0 | 0.5 | benzyldimethyltetra decylammonium chloride | adhesive reaction products were formed on the surface of a slab sample | Comp. Example |
| 2 | 1.0 | 0.5 | sodium benzenesulfonate (1.0) | low resolution | Comp. Example |

TABLE 1-continued

| Class. | Picric acid (wt %) | Cupric chloride (wt %) | Surfactant (wt %) | Solidification structure resolution (after 2 hour-immersion) | Remarks |
|---|---|---|---|---|---|
| 3 | 1.0 | 0.5 | sodium benzenesulfonate (2.0) | low resolution | Comp. Example |
| 4 | 1.0 | 0.5 | sodium benzenesulfonate (3.0) | low resolution | Comp. Example |
| 5 | 1.0 | 0.5 | sodium benzenesulfonate (4.0) | spots were formed on the etched surface of a slab sample by white precipitates | Comp. Example |
| 6 | 1.5 | 0.5 | sodium benzenesulfonate (3.0) | sufficient resolution | Comp. Example |
| 7 | 2.2 | 0.5 | sodium benzenesulfonate (3.0) | spots were formed by insoluble precipitates | Example |
| 8 | 1.5 | 1.0 | sodium benzenesulfonate (3.0) | sufficient resolution | Comp. Example |
| 9 | 1.5 | 1.5 | sodium benzenesulfonate (3.0) | overetched | Comp. Example |

(Remainder: distilled water)

As shown in Table 1, when the amount of picric acid in the etching solution was high, spots were formed by insoluble precipitates, and, when the amount of cupric chloride in the etching solution was high, the slab sample was overetched.

Further, when benzyldimethyltetradecylammonium chloride was used as a surfactant instead of sodium benzene sulfonate, adhesive reaction products are formed on the surface of the slab sample.

Further, when the amount of sodium laurylbenzenesulfonate does not satisfy 1.0~3.0 wt %, there is a problem in that resolution is low or spots are formed on the etched surface of the slab sample.

In contrast, when the etching solution of example 7 was used, a high-resolution image was able to be obtained even when the slab sample is made of low-carbon steel having carbon (C) in an amount of 0.04 wt % or less.

Table 2 shows the results of applying the center segregation evaluating method to a slab sample made of low-carbon steel having carbon (C) in an amount of 0.002 wt % depending on the temperature conditions of an etching solution.

Experimental condition: an etching solution including 1.5 wt % of picric acid, 1.0 wt % of cupric chloride, 3.0 wt % of sodium laurylbenzenesulfonate and a remainder of distilled water was used. A slab sample was immersed in the etching solution for two hours.

TABLE 2

| Class. | Temperature of etching solution (° C.) | Results: determined by solidification structure image (after 2 hour-immersion) | Remarks |
|---|---|---|---|
| 1 | 20 | x | Comp. Example |
| 2 | 30 | ○ | Example |
| 3 | 40 | ○ | Example |
| 4 | 50 | ⊚ | Example |
| 5 | 60 | ⊚ | Example |
| 6 | 70 | ⊚ | Example |
| 7 | 80 | ⊚ | Example |
| 8 | 90 | x | Comp. Example |
| 9 | 100 | x | Comp. Example |

[x: low resolution, ○: sufficient resolution, ⊚: excellent resolution]

As shown in Table 2, the resolution was sufficient when the temperature of the etching solution is 30~80° C., and the resolution was higher when the temperature of the etching solution is 50~80° C.

FIG. 6 (a) shows the result of analyzing a slab made of general steel having sulfur (S) in an amount of 200 ppm using a sulfur printing method, and FIG. 6 (b) shows a slab made of ultra low-sulfur steel having sulfur (S) in an amount of 24 ppm using a sulfur printing method.

As shown in FIG. 6, when the sulfur printing method is used, the center segregation of a slab made of ultra low-sulfur steel having sulfur (S) in an amount of 24 ppm is not visualized, and the resolution of the image is very low, and the solidification structure thereof cannot be observed.

Figure 7:
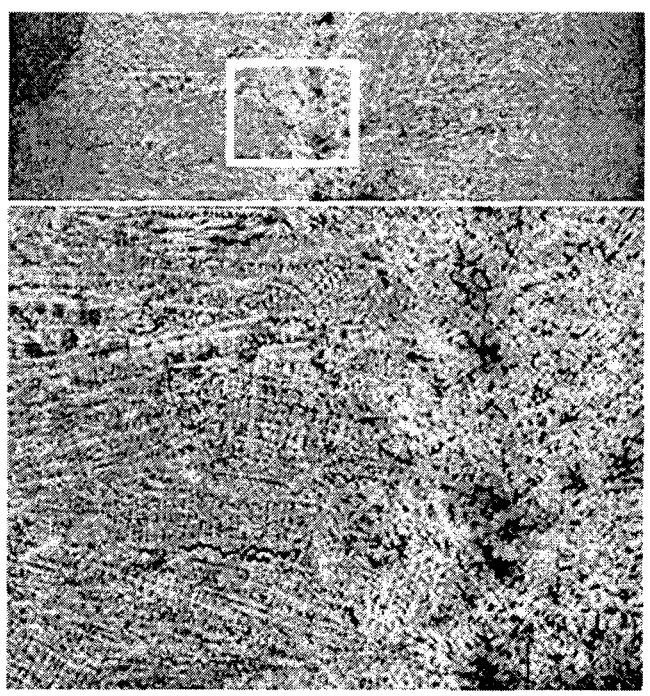
FIG. 7 shows the results of analyzing the section of a slab made of general steel having carbon (C) in an amount of more than 0.04 wt % using a macroetching method.
Figure 9:
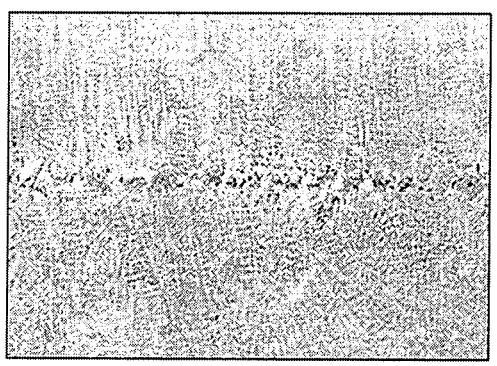
Figure 9:
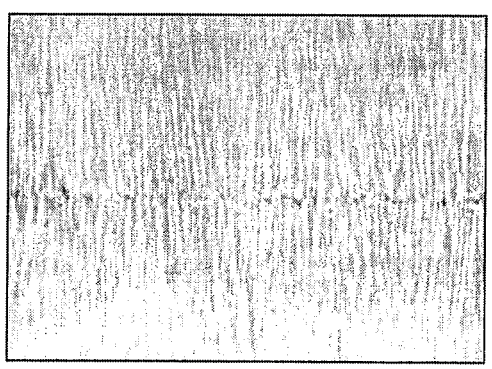

FIG. 7 shows the results of analyzing the section of a slab made of general steel having carbon (C) in an amount of more than 0.04 wt % using a macroetching method; and FIGS. 8 and 9 are views showing the results of analyzing a slab made of medium-carbon steel having carbon (C) in an amount of 0.046 wt % and a slab made of low-carbon steel having carbon (C) in an amount of 0.002 wt % using a macroetching method and a center segregation evaluating method of a second embodiment of the present invention, respectively.

As shown in FIGS. 7 and 8, according to the macroetching method, the center segregation of a slab made of medium-carbon steel having carbon (C) in an amount more than 0.04 wt % can be observed, but it is very difficult to observe the center segregation of a slab made of low-carbon steel having carbon (C) in an amount of 0.04 wt % or less (refer to FIG. 8 (b)).

In contrast, as shown in FIG. 9, when the method of evaluating center segregation of a slab according to the second embodiment of the present invention, the high-resolution center segregation of a slab made of low-carbon steel having carbon (C) in an amount of 0.04 wt % or less is observed (refer to FIG. 9 (b)). Further, the center segregation of a slab made of medium-carbon steel having carbon (C) in an amount of more than 0.04 wt % is also clearly visualized when compared to using the macroetching method (refer to FIG. 9 (a)).

According to the methods of the first and second embodiments of the present invention, the center segregation image of a slab can be quickly visualized even when the slab is made of low-carbon steel having carbon (C) in an amount of 0.04 wt % or less as well as ultra low-sulfur steel having sulfur (S) in an amount of 50 ppm or less, and the condition of the continuous casting process can be checked by the analysis of the visualized center segregation.

In the method of evaluating center segregation of a continuous cast slab according to a third embodiment of the present invention, the center segregation of a slab is visualized into an image using any one of the methods of the first and second embodiments, the image is scanned, and then the center segregation of the slab is evaluated using the Formula discussed below.

The method of the third embodiment is different from the methods of the first and second embodiments in that the method of the third embodiment further includes a process of evaluating the center segregation of a slab using the center segregation image.

The process of evaluating the center segregation of a slab is a process of quantifying the center segregation thereof. The level of the segregation is accurately observed by this process, thus the abnormalities the casting process can be detected.

The center segregation evaluating method uses an index which is called an H-TEC index.

The H-TEC index is calculated by the following Formula: $2.1+(0.15Y-8.7X)/(2.9\times10^7)$. Here, X is the area of center segregated particles, and Y is the area of residual segregated particles other than the center segregated particles.

The correlation coefficient of H-TEC index and EPMA center segregation index is 91% ($R^2=83$), which is high. Therefore, the EPMA method can be replaced by the center segregation evaluating method (refer to FIG. 10).

Specifically, first, the visualized center segregation image is scanned to create an electronic file.

The center segregation image can be visualized using any one of the methods of the first and second embodiments. Since the method of creating the center segregation image is described in detail in the above first and second embodiments, description thereof will be omitted.

After the electronic file is created by scanning the center segregation image, the area of center segregated particles and the area of residual segregated particles other than the center segregated particles are measured, and then the measured values are substituted into the Formula $2.1+(0.15Y-8.7X)/(2.9\times10^7)$ to calculate an H-TEC index. The quantification of center segregation can be conducted by the calculated H-TEC index.

It is possible to check all kinds of steels, including ultra low-sulfur steel and low-carbon steel, using the calculated H-TEC index.

Particularly, in the methods of evaluating center segregation of a continuous cast slab according to the first, second and third embodiments of the present invention, it takes about two hours to form a center segregation image, quantify the center segregation image and evaluate the quantified center segregation image.

When compared to the EPMA method which requires high-priced equipment and a finely-grinded slab and takes much time to treat and analyze a sample, this method can effectively and rapidly evaluate the center segregation of a slab, in particular, the time necessary for evaluating the center segregation thereof using this method is equal to or smaller than ⅙ than the time necessary for evaluating the center segregation using the EPMA method.

Figure 10:
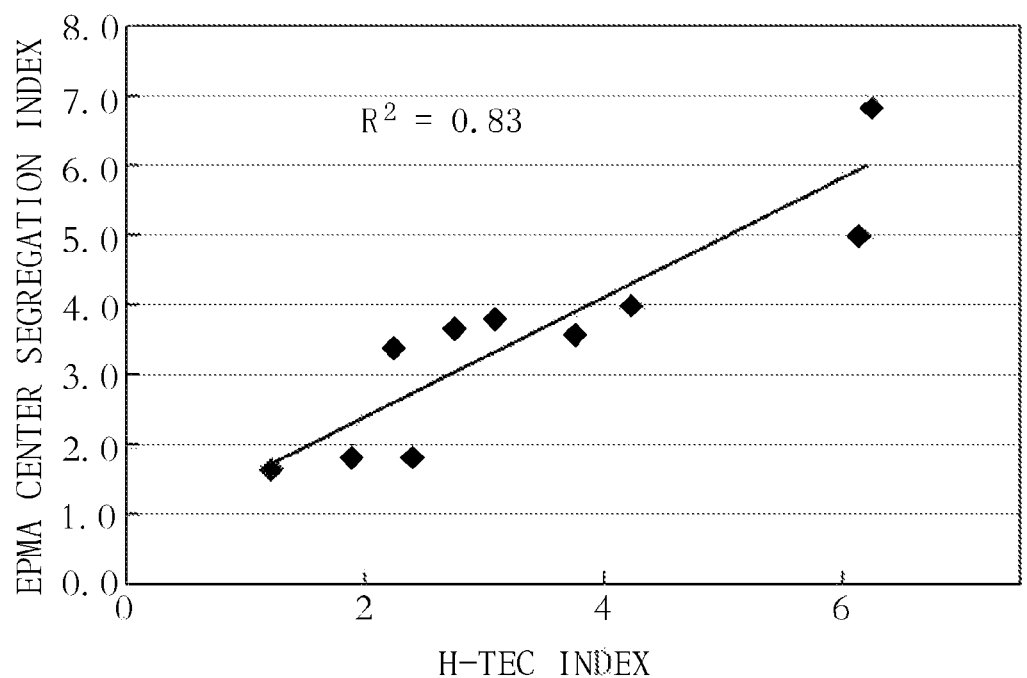
FIG. 10 is a graph showing the relationship between H-TEC index and EPMA center segregation index.

FIG. 10 is a graph showing the relationship between H-TEC index and EPMA center segregation index.

In FIG. 10, the center segregation in the image created by the methods of the first and second embodiments is quantified into H-TEC index, and then the H-TEC index is compared with an EPMA center segregation index.

As shown in FIG. 10, comparing the H-TEC index obtained by quantifying the center segregation image with the EPMA center segregation index, the correlation coefficient of H-TEC index and EPMA center segregation index is 91% ($R^2=83$), which is high.

Accordingly, it is possible to quickly detect the abnormalities occurring when casting ultra low-sulfur steel or low-carbon steel and treat properly the abnormalities.

Although the embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method of determining center segregation of a cast slab, the method comprising:
   providing a slab that includes segregation on a surface thereof, the surface consisting of a central region and a non-central region;
   applying an etching solution onto the surface of the slab for etching the segregation of the surface;
   providing powder to the surface of the slab, whereby the powder is received in recesses formed by etching;
   applying an adhesive sheet over the surface of the slab, whereby at least part of the powder from the recesses is transferred onto the adhesive sheet to form on the adhesive sheet, which represents the segregation of the surface;
   processing the image to determine the area of segregation in the central region and the area of segregation in the non-central region; and
   computing a center segregation index using the following formula:

center segregation index=$a+(b\times Y-c\times X)/d$, wherein X is the area of segregation in the central region, Y is the area of segregation in the non-central region, each of a, b, c and d is a constant greater than 0.

2. The method of claim 1, wherein the etching solution has a temperature of 30 to 80° C.

3. The method of claim 1, wherein the slab comprises carbon (C) in an amount of 0.04 wt % or less.

4. The method of claim 1, wherein the slab comprises sulfur (S) in an amount of 50 ppm or less.

5. The method of claim 1, further comprising applying silicone grease to the surface such that the silicone grease is received in the recesses, wherein the powder is mixed with the silicone grease in the recesses.

6. The method of claim 1, wherein providing powder comprises grinding the surface.

7. The method of claim 1, wherein processing the image comprises:
   measuring the area of segregation in the central region;
   measuring the area of segregation in the non-central region; and
   wherein the formula is as follows:

center segregation index=$2.1+(0.15Y-8.7X)/(2.9\times10^7)$.

8. The method of claim 1, wherein the formula is as follows:

center segregation index=$2.1+(0.15Y-8.7X)/(2.9\times10^7)$.

9. The method of claim 1, wherein, the etching solution comprises picric acid ($C_6H_3N_3O_7$), cupric chloride ($CuCl_2$), sodium laurylbenzenesulfonate ($C_{18}H_{29}SO_3Na$).

10. The method of claim 9, wherein the etching solution further comprises ethanol ($C_2H_5OH$).

11. The method of claim 9, wherein the etching solution comprises:
 the picric acid ($C_6H_3N_3O_7$) in an amount of 1.5 to 2.0 wt %;
 the cupric chloride ($CuCl_2$) in an amount of 0.5 to 1.0 wt %; and
 the sodium laurylbenzenesulfonate ($C_{18}H_{29}SO_3Na$) in an amount of 1.0 to 3.0 wt %.

12. The method of claim 11, wherein the etching solution further comprises ethanol ($C_2H_5OH$) in an amount of 0 vol % to 10 vol %.

* * * * *